United States Patent

Fletcher et al.

[11] Patent Number: 5,302,591
[45] Date of Patent: Apr. 12, 1994

[54] BENZODIAZEPINE DERIVATIVES

[75] Inventors: S. R. Fletcher, Hatfield Heath; V. G. Matassa, Furneux Pelham, both of England

[73] Assignee: Merck Sharpe & Dohme Ltd., Hertfordshire, England

[21] Appl. No.: 54,569

[22] Filed: Apr. 28, 1993

[30] Foreign Application Priority Data

May 1, 1992 [GB] United Kingdom ............... 9209518

[51] Int. Cl.$^5$ ..................... A61K 31/55; C07D 243/24
[52] U.S. Cl. ..................................... 514/221; 540/509
[58] Field of Search ........................ 540/509; 514/221

[56] References Cited

FOREIGN PATENT DOCUMENTS 0284256  9/1988  European Pat. Off. ............ 540/509

OTHER PUBLICATIONS

J. Med. Chem., vol. 32, pp. 13-16, (1989), by Bock, et al., entitled "Benzodiazepine Gastrin and Brain Cholecystokinin Receptor Ligands: L-365,260".

Primary Examiner—Robert T. Bond
Attorney, Agent, or Firm—Robert J. North; Joseph F. DiPrima

[57] ABSTRACT

Compounds of formula (I), and salts and prodrugs thereof

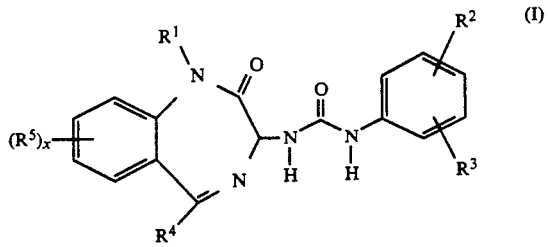

$R^1$ is H, certain optionally substituted alkyl or $C_{3-7}$cycloalkyl;
$R^2$ represents $(CH_2)_m$-tetrazolyl, $(CH_2)_m$-imidazolyl, $CONR^6R^7$, $CONHSO_2R^9$, $SO_2NHCOR^9$, $SOC_{1-4}$alkyl, $SO_2NHR^{10}$, 5-hydroxy-4-pyrone, $(CH_2)_nCO_2H$,

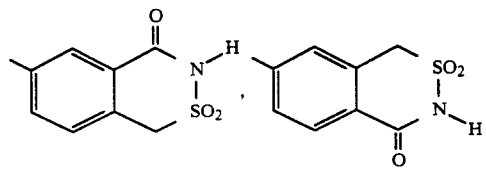

or a group

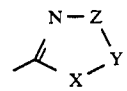

wherein X is O, S or $NR^{11}$; one of Z and Y is C=O and the other is O, S or $NR^{12}$;
$R^3$ represents H or $C_{1-6}$alkyl;
$R^4$ represents 2-, 3- or 4-pyridyl;
$R^5$ represents $C_{1-6}$alkyl, halo or $NR^6R^7$; and
x is 0, 1, 2 or 3;
are CCK and/or gastrin receptor antagonists useful in therapy.

11 Claims, No Drawings

BENZODIAZEPINE DERIVATIVES

This invention relates to benzodiazepine compounds which are useful as antagonists of cholecystokinin and gastrin.

Cholecystokinins (CCK) and gastrin are structurally related peptides which exist in gastrointestinal tissue and in the central nervous system (see, V. Mutt, *Gastrointestinal Hormones*. G. B. J. Green, Ed., Raven Press, N.Y., p.169 and G. Nission, ibid. p.127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide. Trp-Met-Asp-Phe-NH$_2$, which is the common structural element shared by both CCK and gastrin.

CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem* 17, 31, 33 [1982] and references cited therein; J. A. Williams, *Biomed Res.* 3 107 [1982]; and J. E. Morley, *Life Sci.* 30 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholescystokinin receptors termed CCK-A and CCK-B (T. H. Moran et al., "Two brain cholecystokinin receptors: implications for behavioural actions", *Brain Res.*, 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, preferably mammals, and especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; Cervo et. al., 1988, *Eur. J. Pharmacol.*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, B-endorphin, vasopressin and oxytocin, CCK may function as a mediator of responses to stress and as part of the arousal system. CCK-A receptors are now known to be present in a number of areas of the CNS and may be involved in modulating all of the above.

CCK may be involved in the regulation of stress and its relationship with drug abuse e.g. alleviation of the benzodiazepine withdrawal syndrome (Singh et. al., 1992, *Br. J. Pharmacol.*, 105, 8–10) and neuroadaptive processes.

Since CCK and gastrin also have trophic effects on certain tumours [K. okyama, *Hokkaido J. Med. Sci.*, 206–216 (1985)], antagonists of CCK and gastrin are useful in treating these tumours [see, R. D. Beauchamp et al., *Ann. Surg.*, 202, 203 (1985)].

In the light of discussion in C.Xu et al., *Peptides*, 8, 1987, 769–772, CCK antagonists may also be effective in neuroprotection.

CCK receptor antagonists have been found to inhibit the contractile effects of CCK on iris sphincter and ciliary muscles of monkey and human eyes (Eur. J. Pharmacol., 211(2), 183–187; A. Bill et al., Acta Physiol. Scand., 138, 479–485 [1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al., *J. Med Chem.*, 32, 13–16 (1989)].

European patent application no. 0 284 256 discloses benzodiazepine CCK and gastrin receptor antagonists substituted at the 3-position by inter alia, a phenyl urea, and at the 5-position by inter alia a pyridyl group. There is no disclosure of the phenyl urea substitution of the compounds of the present invention.

The present invention provides benzodiazepine compounds of formula (I):

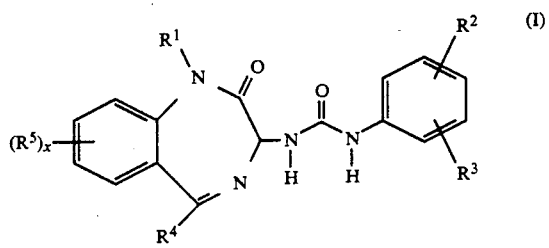

R$^1$ represents H, (CH$_2$)$_q$imidazolyl, (CH$_2$)$_q$tetrazolyl, (CH$_2$)$_q$triazolyl; C$_{1-6}$alkyl optionally substituted by one or more groups selected from halo, hydroxy and $NR^6R^7$; $C_{3-7}$cycloalkyl; cyclopropylmethyl; $CH_2CO_2R^8$, $CH_2CONR^6R^7$ or $CH_2CH(OH)$-W-$(CH_2)_2NR^6R^7$ where W is S or NH;

$R^2$ represents $(CH_2)_m$-tetrazolyl optionally substituted in the tetrazole ring by $C_{1-4}$alkyl, $(CH_2)_m$-imidazolyl, $CONR^6R^7$, $CONHSO_2R^9$, $SO_2NH$-$COR^9$, $SOR^8$, $SO_2NHR^{10}$, 5-hydroxy-4-pyrone, $(CH_2)_nCO_2H$,

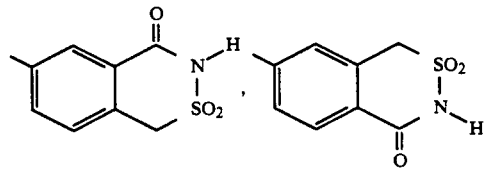

or a group

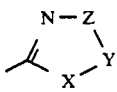

wherein X represents O, S or $NR^{11}$ where $R^{11}$ is H or $C_{1-4}$alkyl; one of Z and Y is C=O and the other is O, S or $NR^{12}$ where $R^{12}$ is H or $C_{1-4}$alkyl;

$R^3$ represents H or $C_{1-6}$alkyl;

$R^4$ represents 2-, 3- or 4-pyridyl;

$R^5$ represents $C_{1-6}$alkyl, halo or $NR^6R^7$;

$R^6$ and $R^7$ each independently represent H or $C_{1-4}$alkyl or $R^6$ and $R^7$ together form a chain $(CH_2)_p$ where p is 4 or 5;

$R^8$ is $C_{1-4}$alkyl;

$R^9$ is $C_{1-6}$alkyl, optionally substituted aryl, 2,2-difluorocyclopropane or trifluoromethyl;

$R^{10}$ represents a nitrogen containing heterocycle;

q is 1, 2 or 3;

m is 0, 1, 2 or 3;

n is 1, 2 or 3;

x is 0, 1, 2 or 3;

and salts and prodrugs thereof.

As used herein, the definition of each expression, when it occurs more than once in any structure, is intended to be independent of its definition elsewhere in the same structure.

It will be appreciated that formula (I) is intended to embrace all possible isomers, including optical isomers, and mixtures thereof, including racemates.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bungaard, Elsevier, 1985.

As used herein, alkyl means linear or branched chain alkyl. Examples of suitable alkyl groups include methyl, ethyl, isopropyl and isobutyl groups.

When $R^1$ represents cycloalkyl, examples of suitable cycloalkyl groups include cyclopropyl, cyclopentyl and cyclohexyl groups, preferably cyclopropyl.

Halo includes fluoro, chloro, bromo and iodo.

Preferably $R^1$ is $C_{1-6}$alkyl, such as methyl, n-propyl or isobutyl. More preferably $R^1$ is methyl.

Suitable examples of the group

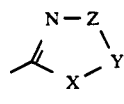

include

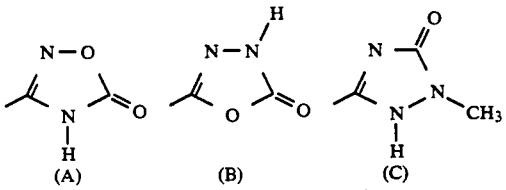

preferably (A).

Suitable values of $R^9$ include methyl, ethyl, i-propyl, t-butyl, optionally substituted phenyl and trifluoromethyl. Where $R^9$ is substituted phenyl, preferably the phenyl substituent is $C_{1-4}$alkyl, more preferably methyl. Preferably $R^9$ is i-propyl or phenyl.

Suitable values for $R^{10}$ include, for example, thiazole, thiadiazole and pyrazine.

Preferably $R^2$ represents $CONHSO_2R^9$ or $SO_2NH$-$COR^9$, more preferably $CONHSO_2R^9$. Particularly preferred are compounds wherein $R^2$ is $CONHSO_2(C_6H_5)$ or $CONHSO_2^iPr$.

Suitable $R^3$ represents H or methyl, preferably H.

Suitable values for $R^5$ include methyl, dimethylamino, chloro and bromo.

Preferably $R^4$ represents 4-pyridyl.

Preferably x is 0.

Preferably the salts of the compounds of formula (I) are pharmaceutically acceptable, but non-pharmaceutically acceptable salts may be used for the preparation of pharmaceutically acceptable salts. The pharmaceutically acceptable salts of the compounds of formula (I) include the conventional non-toxic salts or the quaternary ammonium salts of the compounds from formula (I) formed, e.g., from non-toxic inorganic or organic acids or bases. For example, such conventional non-toxic salts include those derived from inorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic.

The pharmaceutically acceptable salts of the present invention can be synthesized from the compounds of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or combination of solvents.

For example, an acid of formula (I) may be reacted with an appropriate amount of a base, such as an alkali or alkaline earth metal hydroxide e.g. sodium, potassium, lithium, calcium, or magnesium, or an organic base such as an amine, e.g. dibenzylethylenediamine, trimethylamine, piperidine, pyrrolidine, benzylamine, and the like, or a quaternary ammonium hydroxide such as tetramethylammonium hydroxide.

The compounds of formula (I) and their salts and prodrugs, may be administered to animals, preferably to mammals, and most especially to a human subject either alone or, preferably, in combination with pharmaceutically acceptable carriers, optionally with known adjuvants, such as alum, in a pharmaceutical composition, according to standard pharmaceutical practice. The compounds can be administered orally, parenterally, including by intravenous, intramuscular, intraperitoneal or subcutaneous administration, or topically.

The present invention thus provides a pharmaceutical composition comprising a compound of formula (I), or a salt or prodrug thereof, and a pharmaceutically acceptable carrier therefor.

The present invention also provides a process for the preparation of a pharmaceutical composition comprising a compound of formula (I) or a salt or prodrug thereof, which process comprises bringing a compound of formula (I), or a salt or prodrug thereof, into association with a pharmaceutically acceptably carrier.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastro-esophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occurring in association with iritis, ureitis and trauma.

The present invention therefore provides a compound of formula (I) or a salt or prodrug thereof for use in the preparation of a medicament.

The present invention also provides a compound of formula (I) for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 ng/kg to about 1 mg/kg by intravenous administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The compounds of formula (I) may be prepared by processes analogous to those described in European Patent Specification No. 0284256. For example, a compound of formula (I) may be prepared by reaction of an intermediate of formula (II) with a compound of formula (III)

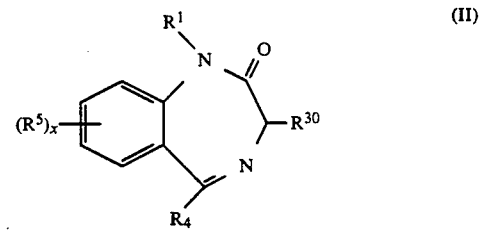

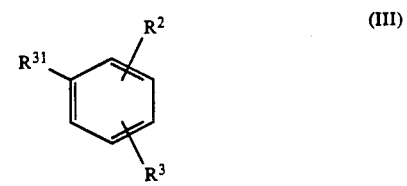

wherein $R^1$, $R^2$, $R^3$, $R^4$, $R^5$ and x are as defined for formula (I), one of $R^{30}$ and $R^{31}$ represents $NH_2$ and the other of $R^{30}$ and $R^{31}$ represents $N{=}C{=}O$ or an activated carbamate.

When one of $R^{30}$ and $R^{31}$ represents $N{=}C{=}O$, the reaction is preferably conducted in a suitable organic solvent, such as an ether, for example, tetrahydrofuran, at room temperature.

When one of $R^{30}$ and $R^{31}$ represents an activated carbamate the reaction is effected in the presence of a base. Suitable bases for use in the reaction include tertiary amines, for example, triethylamine. Preferably $R^{30}$ represents an activated carbamate and $R^{31}$ represents $NH_2$.

The activated carbamate will suitably be an appropriately substituted aryl carbamate, for example

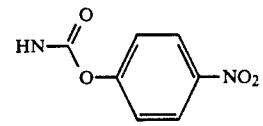

The reaction is conveniently effected in a suitable organic solvent, for example, dimethylformamide, at ambient or elevated temperature. Preferably the reaction is conducted at approximately 50° C.

Intermediates of formula (II) wherein $R^{30}$ is $N{=}C{=}O$ (hereinafter intermediates (IIB)) may be prepared from corresponding amines of formula (II) wherein $R^{30}$ is $NH_2$ (hereinafter intermediates (IIA)) by conventional methods, for example, by treatment with triphosgene.

Intermediates of formula (II) where $R^{30}$ is an activated carbamate (hereinafter intermediates (IIC)) may be prepared from compounds of formula (IIA) by reaction with a suitable chloroformate, for example

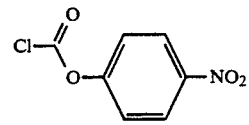

in the presence of a base, such as a tertiary amine, for example, triethylamine.

Intermediates of formula (IIA) may be prepared from compounds of formula (V)

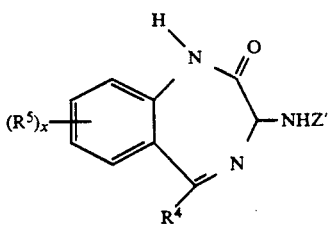 (V)

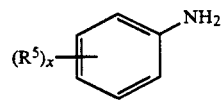 (VIII)

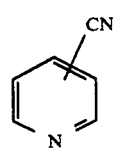 (IX)

wherein $R^4$, $R^5$ and x are as defined for formula (I) and Z' is a protecting group; by reaction with a reagent suitable to introduce the group $R^1$, for example a halide of formula $R^1$Hal where Hal represents halo such as bromo or iodo, in the presence of a base, such as an alkali metal hydride or an alkaline earth metal carbonate, for example sodium hydride or caesium carbonate; or a suitable dialkyl acetal of dimethyl formamide in a suitable organic solvent, e.g. toluene, followed by deprotection.

Compounds of formula (V) may be prepared from compounds of formula (VI)

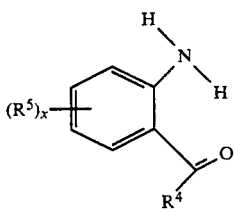 (VI)

wherein $R^4$, $R^5$ and x are as defined for formula (I), by a reaction sequence comprising:

(i) reaction with a compound of formula (VII)

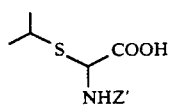 (VII)

wherein Z' is as defined above, in the presence of a base, such as a tertiary amine, for example triethylamine or N-methyl morpholine, and a coupling reagent. Any of the coupling reagents commonly used in peptide synthesis are suitable, for example, 1,3-dicyclohexylcarbodiimide (DCC), isobutyl chloroformate or, preferably, bis(2-oxo-3-oxazolidinyl)phosphonic chloride (BOP-Cl);

(ii) Treatment with gaseous ammonia, preferably in the presence of a mercury containing catalyst, such as mercury(II) chloride. The reaction is conveniently effected in a suitable organic solvent, such as an ether, for example, tetrahydrofuran;

(iii) Treatment with an organic acid, for example acetic or propionic acid, optionally in the presence of an ammonium salt, for example ammonium acetate.

Compounds of formula (VI) may be prepared by known methods, for example, as described in *J. Chem. Soc.*, 1953, 3440; *J. Chem. Soc.*, 1949, 796; or *Can. J. Chem.*, 1965, 944, or by reaction of a compound of formula (VIII) with a pyridine of formula (IX), wherein $R^5$ and x are as previously defined, in the presence of boron trichloride and aluminium chloride.

The reaction is conveniently effected in a suitable organic solvent, such as a halogenated hydrocarbon, for example, 1,1,2,2-tetrachloroethane.

Intermediates of formula (III) wherein $R^{31}$ is N=C=O or an activated carbamate may be prepared from compounds of formula (III) wherein $R^{31}$ is $NH_2$ (hereinafter intermediates (IIIA)) by procedures analogous to those described for the preparation of compounds of formula (IIB) and (IIC).

Amines of formula (IIIA) are known compounds, or may be prepared from the corresponding nitro compounds of formula (X)

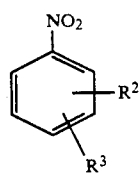 (X)

wherein $R^2$ and $R^3$ are as defined for formula (I), by reduction.

Suitably the reduction is effected by catalytic hydrogenation, for example, using a noble metal catalyst such as palladium which may be supported, e.g. on carbon. The reaction is conveniently effected in a suitable organic solvent, such as an alcohol, e.g. ethanol.

Compounds of formula (X) are commercially available or may be prepared by the procedures described in the accompanying Examples or by alternative procedures which will be readily apparent to one skilled in the art.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

Enantiospecific synthesis of compounds of formula (I) may be achieved, for example, by reaction of chiral intermediates of formula (II), which chiral intermediates may be prepared from the corresponding racemate by conventional procedures, for example, as described in *J. Org. Chem.*, 52, 955 and 3232, (1987), with compounds of formula (III).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following examples are provided to assist in a further understanding of the invention. Particular materials employed, species and conditions are intended to be further illustrative of the invention and not limitative of the scope thereof.

EXAMPLE 1

N-[3(R,S)-2,3-Dihydro-1-methyl-2-oxo-5-(pyridin-4-yl)-1H-1,4-benzodiazepin-3-yl]-N'-[3-(phenylsulphonylaminocarbonyl) phenyl]urea Step A: (2-Aminophenyl)-(pyridin-4-yl)methanone A 1M solution of boron trichloride (in dichloromethane, 130 ml, 130 mmol) was added dropwise to a stirred, cooled (0° C.) solution of aniline (10.92 ml, 120 mmol) in 1,1,2,2-tetrachloroethane (160 ml). After addition a solution of 4-cyanopyridine (16.63 g, 160 mmol) in 1,1,2,2-tetrachloroethane (240 ml) was added followed by solid aluminium trichloride (17.33 g, 130 mmol) and further 1,1,4,4-tetrachloroethane (100 ml). The reaction mixture was heated to 100° C. for 6 hours, cooled to 0° C. then treated cautiously with 2M hydrochloric acid (100 ml). After addition the mixture was heated at 100° C. for 30 minutes, cooled to room temperature then basified with 2M sodium hydroxide solution. The organic layer was separated and the aqueous exhaustively extracted with dichloromethane. The combined organics were dried (sodium sulphate) and evaporated to give the crude product which was triturated with propan-2-ol to afford the title compound as a yellow solid (8.22 g, 35%). mp 153°–161° C.; IR (nujol) 1620 cm$^{-1}$; $^1$H NMR (250MHz, CDCl$_3$) δ 6.30 (2H, broad s), 6.60 (1H, ddd, J$_1$=1Hz, J$_2$=J$_3$=8Hz), 6.73 (1H, dd, J$_1$=1Hz, J$_2$=8Hz), 7.29–7.37 (2H, m), 7.43 (2H, dd, J$_1$=2Hz, J$_2$=4.5Hz), 8.75 (2H, dd, J$_1$=2Hz, J$_2$=4.5Hz).

Step B: 3(R,S)-Amino-1,3-dihydro-1-methyl-5-(pyridil-4-yl)-2H-1,4-benzodiazepin-2-one To a stirred, cooled (0° C.) solution of α-(isopropylthio)-N—-(benzyloxycarbonyl)glycine (16.64 g, 0.0588 mol) in anhydrous dichloromethane (400 ml), under a nitrogen atmosphere, was added dropwise a solution of N-methylmorpholine (6.46 ml, 0.0588 mol) in anhydrous dichloromethane (20 ml), followed by a solution of isobutylchloroformate (7.63 ml, 0.0588 mol) in anhydrous dichloromethane (50 ml). The solution was stirred at 5° C. for 30 minutes then heated to reflux. (2-Aminophenyl)-(pyridin-4-yl)methanone (11.1 g, 0.056 mol) in anhydrous dichloromethane (100 ml) was added dropwise and the resulting reaction mixture heated at reflux for 30 minutes then at room temperature for 18 hours. The reaction mixture was washed with 10% citric acid then with 10% sodium hydrogen carbonate solution. The organic layer was dried (magnesium sulphate) then evaporated to give a gum.

The crude (isopropylthio)glycinamide was dissolved in anhydrous tetrahydrofuran (500 ml) and the ice cooled solution was saturated with ammonia gas. Mercuric chloride (15.96 g, 0.059 mol) was added and the passage of ammonia continued for a further 1 hour. The mixture was filtered and the filtrate concentrated then triturated with petroleum ether (60–80). The resulting crude product was dissolved in glacial acetic acid (400 ml), treated with ammonium acetate (16 g) and the mixture was stirred at ambient temperature for 18 hours. The solvent was evaporated and the residue partitioned between ethyl acetate and 4M sodium hydroxide. The organic layer was separated, dried (sodium sulphate), then evaporated to dryness. The crude product was purified by column chromatography on silica using dichloromethane—10% methanol/dichloromethane (gradient) to afford starting aminoketone (6.82 g, 61%) followed by 3(R,S)-(benzyloxycarbonylamino)-1,3-dihydro-5-(pyridin-4-yl)-2H-1,4-benzodiazepin-2-one (1.96 g, 9%).

The foregoing benzodiazepine (1.96 g, 4.92 mmol) was dissolved in anhydrous dimethylformamide (65 ml) and cooled to 0° C. Sodium hydride (214 mg of a 55% oil dispersion, 4.92 mmol) was added and the mixture stirred for 40 minutes at 0° C. Iodomethane (306 μl, 4.92 mmol) was added and the mixture stirred at room temperature for 3 hours then evaporated to dryness. The residue was partitioned between ethyl acetate (75 ml) and water (50 ml). The organic layer was separated then the aqueous re-extracted with ethyl acetate (2×50 ml). The combined organics were dried (magnesium sulphate), evaporated to dryness then purified by column chromatography on silica using 5% methanol in dichloromethane to afford 3(R,S)-(benzyloxycarbonylamino)-1,3-dihydro-1-methyl-5-(pyridin-yl)-2H-1,4-benzodiazepin-2-one (1.33 g, 68%).

The foregoing benzodiazepine (1.0 g, 2.5 mmol) in glacial acetic acid (30 ml) was treated with hydrogen bromide in acetic acid (45% w/v, 4.5 ml, 25 mmol). After 4 hours cold diethyl ether (200 ml) was added and the solid filtered off. This solid was dissolved in 10% potassium carbonate solution (50 ml) then extracted with dichloromethane (6×50 ml). The combined organics were dried (sodium sulphate)then evaporated to afford 3(R,S)-amino-1,3-dihydro-1-methyl-5-(pyridin-4-yl)-2H-1,4-benzodiazepin-2-one (0.615 g, 92%) as a foam. Rf=0.40 in dichloromethane/methanol (9:1) on silica plates; $^1$H NMR (360MHz, CDCl$_3$)δ2.22 (2H, broad s), 3.48 (3H, s), 4.51 (1H, s), 7.22–7.31 (2H, m), 7.40 (1H, d, J=8Hz), 7.53 (2H, dd, J$_1$=1.5, J$_2$=4.5Hz), 7.62 (1H, ddd, J$_1$=2, J$_2$=J$_3$=8Hz), 8.70 (2H, dd, J$_1$=1.5, J$_2$=4.5Hz).

Step C: 3-(Phenylsulphonylaminocarbonyl)aniline

Benzenesulphonamide (9.4 g, 60 mmol), 3-nitrobenzoic acid (10.0 g, 60 mmol), 4-dimethylaminopyridine (7.32 g, 60 mmol) and 1-[3-(dimethylamino)propyl]-3-ethylcarbodiimide hydrochloride (11.48 g, 60 mmol) were stirred in anhydrous dichloromethane (400 ml) for 2 hours. The reaction mixture was extracted with 1M sodium hydroxide solution (300 ml), aqueous separated then re-acidified to pH=3 with 5M hydrochloric acid. 3-Nitro-(phenylsulphonylaminocarbonyl)benzene was isolated as a colourless solid (16.0 g, 87%), mp 186°–188° C.

A suspension of the foregoing nitro compound (14.8 g, 48 mmol) in ethanol (240 ml) was hydrogenated over 10% palladium on carbon (1.4 g) at 45 psi for 1.5 hours. The reaction mixture was filtered then evaporated and the crude product recrystallised from hot ethanol to afford 3-(phenylsulphonylaminocarbonyl)aniline (10.57 g, 80%) as a colourless crystalline solid, mp 138° C. Rf=0.42 in dichloromethane/methanol (9:1) on silica plates.

Step D: N-[3(R,S)-2,3-Dihydro-1-methyl-2-oxo-5-(pyridin-4-yl)-1H-1,4-benzodiazepin-3-yl]-N'-[3-(phenylsulphonylamino carbonyl)phenyl]urea To a stirred, cooled (4° C.) solution of 3(R,S)-amino-1,3-dihydro-1-methyl-5-(pyridin-4-yl)-2H-1,4-benzodiazepin-2-one (610 mg, 2.29 mmol) in anhydrous tetrahydrofuran (15 ml), under a nitrogen atmosphere, was added triethylamine (319 µl, 2.29 mmol) followed by a solution of p-nitrophenylchloroformate (462 mg, 2.29 mmol) in anhydrous tetrahydrofuran (15 ml). The reaction mixture was then stirred at ambient temperature for 3.5 hours, filtered then evaporated then triturated with diethyl ether to give the crude carbamate (920 mg, 93%).

To a solution of this carbamate (347 mg, 0.804 mmol) in anhydrous dimethylformamide (4 ml) was added triethylamine (112 µl, 0.804 mmol). After 5 minutes a solution of 3-(phenylsulphonylaminocarbonyl)aniline (233 mg, 0.804 mmol) in anhydrous dimethylformamide (5 ml) was added then the reaction mixture was heated at 50° C. for 2 hours. The solvent was evaporated and the residue was partitioned between ethyl acetate (20 ml) and 20% aqueous acetic acid (10 ml). Organic layer was separated, aqueous further extracted with ethyl acetate (4×20 ml), dried (sodium sulphate) then evaporated to dryness. The crude product was recrystallised from ethanol to afford the title compound as a cream solid (110 mg, 24%), mp>240° C. (dec.). Rf=0.40 in 10% methanol/dichloromethane on silica plates; $^1$H NMR (360MHz, DMSO-d$_6$)δ3.41 (3H, s), 5.28 (1H, d, J=8Hz), 7.34-7.90 (14H, m), 7.98 (2H, dd, J$_1$=1.5, J$_2$=7Hz), 8.68 (2H, d, J=7Hz), 9.27 (1H, s). Found: C, 60.46; H, 4.38; N, 14.60. C$_{29}$H$_{24}$N$_6$O$_5$S.0.5H$_2$O requires C, 60.30; H, 4.36; N, 14.55%.

EXAMPLE 2

N-[3(R,S)-2,3-Dihydro-1-methyl-2-oxo-5-(pyridin-4-yl)-1H-1,4-benzodiazepin-3-yl)-N'-[3-(isopropylsulphonylaminocarbonyl) phenyl]urea The title compound was obtained (112 mg, 30%) from 3-(R,S)-amino-1,3-dihydro-1-methyl-5-(pyridin-4-yl)-2H-1,4-benzodiazepin-2-one (Example 1, Step B) and 3- (isopropyl sulphonylaminocarbonyl)aniline (prepared from isopropyl sulphonamide and 3-nitrobenzoic acid using the procedure described in Example 1, Step C), using the procedure described in Example 1, Step D. mp>216° C. (dec.)(ethanol). Rf=0.35 in 10% methanol/dichloromethane on silica plates; $^1$H NMR (360MHz, DMSO-d$_6$)δ1.30 (6H, d, J=7Hz), 3.42 (3H, s), 3.78-3.83 (1H, m), 5.30 (1H, d, J=8Hz), 7.35-7.96 (11H, m), 8.68 (2H, d, J=7Hz), 9.30 (1H, s), 11.60 (1H, broad s). Found: C, 57.82; H, 5.05; N, 15.54. C$_{26}$H$_{26}$N$_6$O$_5$S.0.25H$_2$O requires C, 57.93; H, 4.95; N, 15.59%.

| EXAMPLE 3A Tablets containing 1-25 mg of compound | | | |
|---|---|---|---|
| | Amount mg | | |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

| EXAMPLE 3B Tablets containing 26-100 mg of compound | | | |
|---|---|---|---|
| | Amount mg | | |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

| EXAMPLE 4 Parenteral injection | |
|---|---|
| | Amount mg |
| Compound of formula (I) | 1 to 100 |
| Citric Acid Monohydrate | 0.75 |
| Sodium Phosphate | 4.5 |
| Sodium Chloride | 9 |
| Water for Injections | to 1 ml |

The sodium phosphate, citric acid monohydrate and sodium chloride are dissolved in a portion of the water. The compound of formula (I) is dissolved or suspended in the solution and made up to volume.

| EXAMPLE 5 Topical formulation | |
|---|---|
| | Amount mg |
| Compound of formula (I) | 1-10 |
| Emulsifying Wax | 30 |
| Liquid paraffin | 20 |
| White Soft Paraffin | to 100 |

The white soft paraffin is heated until molten. The liquid paraffin and emulsifying wax are incorporated and stirred until dissolved. The compound of formula (I) is added and stirring continued until dispersed. The mixture is then cooled until solid.

BIOLOGICAL ACTIVITY

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 83, 4923-4926, 1986) with minor modifications.

Male Sprague-Dawley rats (150-200 g) were sacrificed by decapitation. The whole pancreas was dissected free of fat tissue and was homogenized in 25 volumes of ice-cold 10 mM N-2-hydroxyethyl-piperazine-N'-2-ethane sulphonic acid (HEPES) buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20 mM (HEPES)), 1 mM ethylene glycol-bis-(β-aminoethylether-N,N'-tetraacetic acid) (EGTA), 5 mM MgCl₂, 150 mM NaCl, bacitracin 0.25 mg/ml, soya bean trypsin inhibitor 0.1 mg/ml, and bovine serum albumin 2 mg/ml pH 6.5 at 25° C.) using a Teflon (trademark) homogenizer, 15 strokes at 500 rpm. The homogenate was further diluted in binding assay buffer to give a final concentration of 0.5 mg original wet weight/1 ml buffer. For the binding assay, 50 μl of buffer (for total binding) or unlabelled CCK-8 sulphated to give a final concentration of 1 μM (for nonspecific binding) or the compounds of Formula I (for determination of inhibition of $^{125}$I-CCK-8 binding) and 50 μl of 500 pM $^{125}$I-CCK-8 (i.e. 50 pM final concentration) were added to 400 μl of the membrane suspensions in microfuge tubes. All assays were run in duplicate. The reaction mixtures were incubated at 25° C. for 2 hours and the reaction terminated by rapid filtration (Brandell 24 well cell harvester) over Whatman GF/C filters, washing 3×4 mls with ice-cold 100 Mm NaCl. The radioactivity on the filters was counted with a LKB gamma counter.

2. CCK Receptor Binding (Brain)

CCK-8 sulphated was radiolabelled and the binding was performed according to the description for the pancreas method with minor modifications.

Male Hartley guinea pigs (300–500 g) were sacrificed by decapitation and the cortex was removed and homogenized in 25 mL ice-cold 0.32M sucrose. The homogenates were centrifuged at 1000 g for 10 minutes and the resulting supernatant was recentrifuged at 20,000 g for 20 minutes. The P₂ pellet was resuspended in binding assay buffer (20 mM HEPES, 5 mM MgCl₂, 0.25 mg/ml bacitracin, 1 mM EGTA pH 6.5 at 25° C.), using a Teflon (trademark) homogenizer (5 strokes at 500 rpm) to give a final concentration of 10 mg original wet weight/1.2 ml buffer. For the binding assay, 50 μl of buffer (for total binding) or unlabelled CCK-8 sulphated to give a final concentration of 1 μM (for nonspecific binding) or the compounds of Formula I (for determination of inhibition of $^{125}$I-CCK-8 binding) and 50 μl of 500 pM $^{125}$I-CCK-8 (i.e. final concentration of 50 pM) were added to 400 μl of the membrane suspensions in microfuge tubes. All assays were run in duplicate. The reaction mixtures were incubated at 25° C. for 2 hours and then the reaction was terminated by rapid filtration (Brandell 24 well cell harvester) on Whatman GF/C filters with 3×5 ml washes of cold 100 mM NaCl. The radioactivity on the filters was counted with a LKB gamma counter.

In Vitro Results Effects of the Compounds of Formula I on $^{125}$I-CCK-8 Receptor Binding The preferred compounds of Formula I are those which produced dose-dependent inhibition of specific $^{125}$I-CCK-8 binding as defined as the difference between total and non-specific (i.e. in the presence of 1 μM CCK) binding.

Drug displacement studies were performed with at least 10 concentrations of compounds of Formula I and the IC₅₀ values were determined by regression analysis IC₅₀ refers to the concentration of the compound required to inhibit 50% of specific binding of $^{125}$I-CCK-8.

The data in Table I were obtained for compounds of Formula I.

TABLE I

| CCK RECEPTOR BINDING RESULTS IC₅₀(nM) | | |
|---|---|---|
| Compound of Ex # | $^{125}$I-CCK Pancreas | $^{125}$I-CCK Brain |
| 1 | 790 | 130 |
| 2 | 1630 | 300 |

We claim:

1. A compound of formula (I), or a pharmaceutically acceptable salt or prodrug thereof:

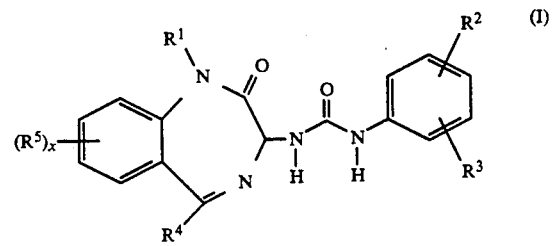

wherein:
R¹ is selected from the group consisting of H, (CH₂)qimidazolyl, (CH₂)qtetrazolyl, (CH₂)qtriazolyl; C₁₋₆alkyl; C₁₋₆alkyl substituted by at least one group selected from halo, hydroxy and NR⁶R⁷; C₃₋₇cycloalkyl; cyclopropylmethyl; CH₂CO₂R⁸, CH₂CONR⁶R⁷ and CH₂CH(OH)-W-(CH₂)₂NR⁶R⁷ where W is S or NH;

R² is selected from the group consisting of (CH₂)m-tetrazolyl, (CH₂)m-tetrazolyl substituted in the tetrazole ring by C₁₋₄alkyl, (CH₂)m-imidazolyl, CONR⁶R⁷, CONHSO₂R⁹, SO₂NHCOR⁹, SOR⁸, SO₂NHR¹⁰, 5-hydroxy-4-pyrone, (CH₂)nCO₂H,

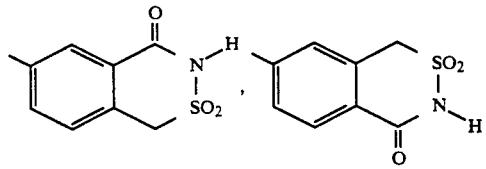

and

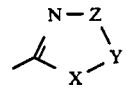

wherein X is selected from the group consisting of O, S and NR¹¹ where R¹¹ is selected from the group consisting of H and C₁₋₄alkyl; one of Z and Y is C=O and the other is selected from the group consisting of O, S and NR¹² where R¹² is selected from the group consisting of H and C₁₋₄alkyl;

R³ is selected from the group consisting of H and C₁₋₆alkyl;

R⁴ represents pyridyl;

R⁵ is selected from the group consisting of C₁₋₆alkyl, halo and NR⁶R⁷;

R⁶ and R⁷ are each independently selected from H or C₁₋₄alkyl or R⁶ and R⁷ together form a chain (CH₂)p where p is 4 or 5;

R⁸ is C₁₋₄alkyl;

$R^9$ is selected from the group consisting of $C_{1-6}$alkyl, unsubstituted aryl, $C_{1-4}$alkyl substituted aryl, 2,2-difluorocyclopropane and trifluoromethyl;

$R^{10}$ represents a nitrogen containing heterocycle selected from thiazole, thiadiazole, or pyrazine;

q is selected from 1, 2 and 3;

m is selected from 0, 1, 2 and 3;

n is selected from 1, 2 and 3; and x is selected from 0, 1, 2 and 3.

2. A compound as claimed in claim 1 where $R^1$ is $C_{1-6}$alkyl.

3. A compound as claimed in claim 1 wherein $R^2$ is selected from the group consisting of $CONHSO_2R^9$ and $SO_2NHCOR^9$.

4. A compound as claimed in claim 3 wherein $R^9$ is selected from the group consisting of $C_{1-6}$alkyl, phenyl, $C_{1-4}$alkyl substituted phenyl or trifluoromethyl.

5. A compound as claimed in claim 1 wherein $R^4$ is 4-pyridyl.

6. A compound as claimed in claim 1 selected from:

N-[3-(R,S)-2,3-dihydro-1-methyl-2-oxo-5-(pyridin-4-yl)-1H-1,4-benzodiazepin-3-yl]-N'-[3-(phenylsulphonyl aminocarbonyl)phenyl]urea;

N-[3-(R,S)-2,3-dihydro-1-methyl-2-oxo-5-(pyridin-4-yl)-1H-1,4-benzodiazepin-3-yl]-N'-[3-(isopropylsulphonyl aminocarbonyl)phenyl]urea;

and pharmaceutically acceptable salts and prodrugs thereof.

7. A pharmaceutical composition comprising a pharmaceutically effective amount of a compound according to claim 1 in association with a pharmaceutically acceptable carrier or excipient.

8. A method for the treatment or prevention of a physiological disorder involving CCK and/or gastrin, which method comprises administration to a patient in need thereof of a CCK and/or gastrin reducing amount of a compound according to claim 1.

9. A method as claimed in claim 8 for the treatment or prevention of anxiety.

10. A method as claimed in claim 8 for the treatment or prevention of panic.

11. A method as claimed in claim 8 for the treatment of pain.

* * * * *